United States Patent [19]

Petersen

[11] Patent Number: 4,567,886
[45] Date of Patent: Feb. 4, 1986

[54] FLEXION SPACER GUIDE FOR FITTING A KNEE PROSTHESIS

[76] Inventor: Thomas D. Petersen, 9680 Alto Dr., La Mesa, Calif. 92041

[21] Appl. No.: 455,905

[22] Filed: Jan. 6, 1983

[51] Int. Cl.⁴ .............................................. A61F 5/04
[52] U.S. Cl. ............................... 128/92 H; 128/92 E
[58] Field of Search ............. 128/92 H, 92 C, 92 CA, 128/92 R, 303 R, 92 E

[56] References Cited

U.S. PATENT DOCUMENTS

| D. 245,918 | 9/1977 | Shen | 128/92 EB |
| 4,409,973 | 10/1983 | Neufeld | 128/92 E |
| 4,457,307 | 7/1984 | Stillwell | 128/92 E |

OTHER PUBLICATIONS

Zimmer, "EFTEKHAR TM II Knee Prosthesis", 1980, B-2815M281.
Zimmer, "Sheehan Knee Prosthesis Broad Condyle Model", 1981, 81-038-8454-0906/2MZ.
Zimmer, "The Multi-Radius TM Total Knee w/Surgeon-Guided Instrumentation", 1978, B-271, 7500M680.
Zimmer, "Geo-Patella TM /Geo Tibial TM Total Knee", 1977, B-268-1, 10M778.
Dow Corning Wright "Whiteside Ortholoc TM Total Knee System", 1983, L095-0101.
Dow Corning Wright, "Lacey Condylar Total Knee System", 1983, L095-0104.
Zimmer, "Knee Replacement Using the Insall/Burstein Total Condylar Knee System", 1980, B-251-2, ISM181.
Zimmer, "Multi-Radius TM Total Knee", 1978, B272, 2M179.
Howmedica, "Variable Axis TM Total Knee Surg. Tech.", Murray, ST2001-1, 1/80, 10M.
Howmedica, "The Howmedica® Kinematic TM Knee System", Thomas, 1981, ST3210-1, 2/81 ISM B.
Richards, "R.M.C. TM Total Knee System", 1978, 3246.
Howmedica, "Total Condylar Prosthesis Surg. Tech.", Insall & Ranawat, 1976, ST 2002, 12/76 10M.
Howmedica, "Variable Axis TM Total Knee Surg. Tech.", Murray, 1977, ST2001, 1/77 10M.
Howmedica, "Total Condylar Knee Prosthesis Surg. Tech.", Insall, 1978, ST2011, 12/78 10MB.
Howmedica, "Total Condylar Knee Prosthesis Surg. Tech.", Ranawat, 1978, ST2010, 2/79 10MB.
Zimmer, "Cloutier TM Total Knee" Surgical Technique, 1979, B-274 5M679.
Zimmer, "Cloutier TM II Total Knee" Surgical Technique, 1981, 81-038, 5701-0968/5MZ.
Richards, "R.M.C. ® Total Knee System", 1983, 4997.
Howmedica, "Universal Total Knee Instrument System", 1980, H-2026, 2/81 ZOM B.

Primary Examiner—Gene Mancene
Assistant Examiner—C. W. Shedd
Attorney, Agent, or Firm—Sherman & Shalloway

[57] ABSTRACT

A spacer guide for utilization in total knee surgery for establishing size of prosthesis and position of cuts for total knee replacement surgery includes a generally L-shaped base member for attachment to the anterior femoral cortex of a prepared femur with a generally L-shaped adjustable support member adjustably secured to the base support member and a vertically positionable indicator slide having a squaring jig for cooperative engagement and alignment with the cutting head of a tibia alignment and resection guide for squaring the tibia and femur and including indicator means for indicating the position of a tibia plateau cut and indicating the size and positioning for a distal femoral cut for indicating the sizing of both the tibial and femoral prostheses.

11 Claims, 3 Drawing Figures

FLEXION SPACER GUIDE FOR FITTING A KNEE PROSTHESIS

BACKGROUND OF THE INVENTION

The present invention relates to surgical instruments and pertains particularly to a spacer guide for utilization in total knee surgical techniques.

In my prior application entitled "Surgical Knee Alignment Method and System", Ser. No. 337,587 now U.S. Pat. No. 4,524,766, filed Jan. 7, 1982, I disclose methods and instrumentation for accomplishing total knee surgery. One instrument disclosed in that system is a posterior spacer guide which was utilized after a resection of the tibia plateau to indicate the two prostheses for the particular knee under consideration. That instrument, however, was subject to errors if the tibia was not held in tension at precisely 90° of flexion.

The instrument of the present application is an improvement of that instrument and is utilized in conjunction with a tibial resector guide to assure proper 90° alignment as well as to the appropriate proximal tibial cut, distal femoral cut and the proper tibial and femoral prostheses.

SUMMARY AND OBJECTS OF THE INVENTION

It is therefore the primary object of the present invention to provide an improved spacer guide.

In accordance with the primary aspect of the present invention, a spacer guide includes a base member for attachment to a prepared femur with adjustable means for adjusting and positioning the instrument for engagement with a tibia resection guide for indicating proper tibia alignment and including indicator means for indicating the proper tibia prosthesis and the femoral prosthesis.

BRIEF DESCRIPTION OF THE DRAWINGS

The above and other objects and advantages of the present invention will become apparent from the following description when read in conjunction with the drawings wherein.

DETAILED DESCRIPTION OF A PREFERRED EMBODIMENT

Figure 1:
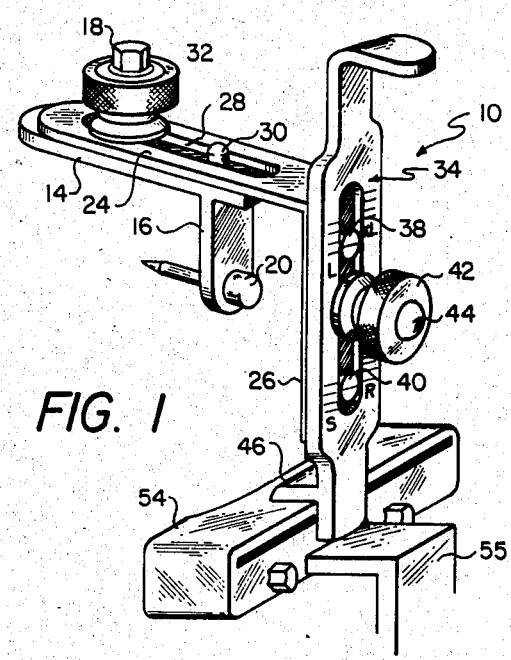
FIG. 1 is a perspective view of a preferred embodiment of the present invention.
Figure 3:
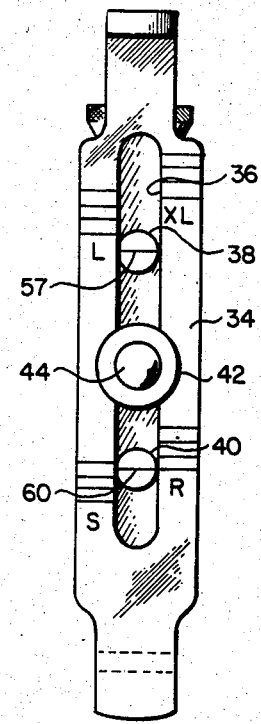
FIG. 3 is a front elevation view of the spacer guide of FIG. 1.
Figure 2:
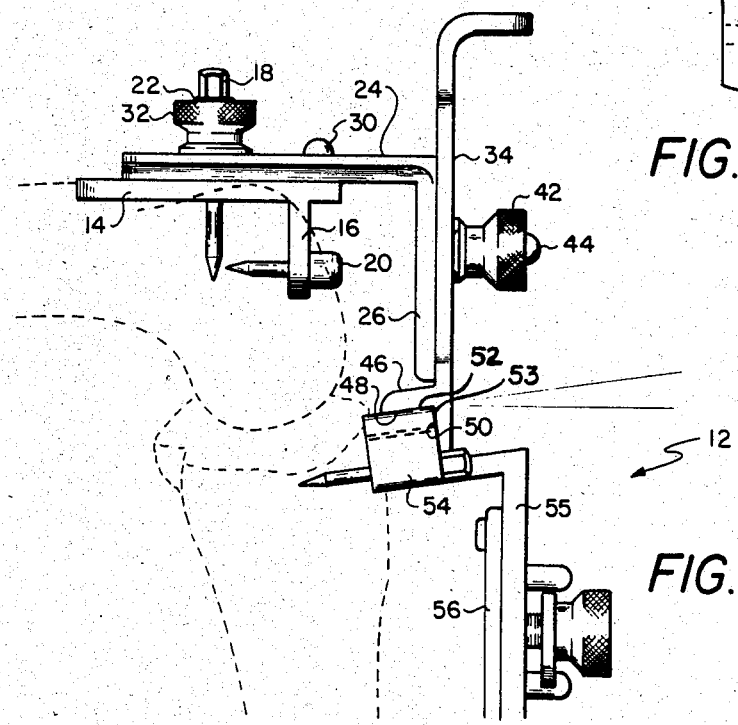
FIG. 2 is a side elevation view of the embodiment of FIG. 1 shown in conjunction with a tibia resection guide.

Referring to FIG. 1 of the drawing, a spacer guide in accordance with the invention designated generally by the numeral 10 is shown in use in conjunction with a tibia resection guide designated generally by the numeral 12 as disclosed in my aforementioned patent application. The spacer guide includes a generally L-shaped base support member comprising a generally horizontal leg or arm member 14 and a generally vertical foot or arm member 16 extending downward at 90° from the horizontal member 14. The horizontal member 14 is designed to fit within a prepared surface of a femoral cortex and align generally with the axis of a femur. The base member is secured in position or anchored to the femoral cortex by means of anchoring pins 18 and 20. The pin 18 extends through a coaxial central bore of a stud 22 secured to the leg 14 of the base member. The fixed pin 20 extends in the foot or arm portion or member 16 of the base member.

A generally L-shaped movable support member is adjustably mounted on the base support member for longitudinal adjustment along member 14, and includes a generally horizontal arm 24 and a vertical arm 26 extending downward at 90° to the horizontal arm. The horizontal arm 24 includes a slot 28 cooperatively engaging the stud 22 and a guide pin 30 for longitudinal adjustment on the horizontal leg member 14. A thumb screw or wing nut 32 threadably mounted on the hollow stud 22 clamps and movable support member 24 to the horizontal leg 14 of the fixed support member. This permits selective adjustment and positioning of the movable support member 24, 26 axially of the femur to accommodate various anatomical variations in bone structure. It also permits the vertical and horizontal positioning of the indicator slide of the instrument to cooperate with the tibia resection guide for appropriate alignment and positioning.

A vertical slide member 34 includes a vertical guide slot 36 for cooperatively engaging a pair of spaced guide pins or studs 38 and 40 securely mounted on the vertical leg 26 of the movable support member. A thumb nut or screw 42 is mounted on a stud 44 mounted on the vertical leg member 26 for clamping the vertical slide member 34 in selected positions relative to the vertical leg member 26.

The slide member 34 is provided with a squaring jig including a foot member 46 having an alignment surface 48 which also cooperates with adjacent alignment surface 50 for engagement with the squaring surfaces 52 and 53 of a cutting guide head 54 of a tibia resection guide 55. The alignment and squaring jig surfaces 48 and 50 are angled at an appropriate angle to the slope of the cutting guide surfaces 52 and 53 of the tibia cutting guide head 54. This angle of surface 52 may vary from about 0° to up to about 10° to the horizontal. When the surfaces 48 and 50 align with the surfaces 52 and 53 of the cutting guide head 54, and the cutting guide head are appropriately positioned and aligned for the appropriate cut on the tibia, the tibia is at a 90° flexion with the femur for the most accurate establishment and determination of the spacing between the prepared surfaces of the tibia and posterior femoral cortex.

The spacer guide is provided with appropriate indicator means which indicates by appropriate indicia the available sizes of tibia and femur prostheses.

The distance from the anterior femoral cortex to the cut surface of the tibia will be determined with the ligaments held in tension at 90° of flexion. The distance is calibrated on the indicator to reflect the size of the prosthesis as related to the anterior femoral cortex.

The tibia cutting guide includes the head 54 mounted on an extensible frame including an upper member 55 slidably mounted in telescopic relation with a lower member 56. The lower member (only part of which is shown) extends downward and engages the tibia near the ankle for proper alignment of the instrument for the proper cut of the tibia plateau, as explained in my prior application.

The indicator means of the present instrument includes an indicator line 57 on the upper guide pin 38 and an indicator line 60 on the lower guide pin 40. These indicator lines cooperate with the various scales, labeled S, R, L, and XL on the slide member 34 to indicate the proper tibia plateau for the particular prosthesis. Alignment of a particular one of the indicator lines 57 and 60 with a proper one of the scale lines indicates the respective prosthesis size.

In operation, a femur which has been prepared for surgery is further prepared by surfacing the intercondyle surface by filing or the like to mount the base support member 14, 16 with the horizontal leg member 14 extending and lying within the prepared intercondyle surface to properly align the member with the axis and anterior cortex of the femur. The base member is then attached in position by driving the pins 28 and 20 into the femoral condyle to anchor the member in position. The clamp nut 32 is left sufficiently loose to permit the leg member 24 to slide horizontally to properly position the vertical slide member 34 with respect to a tibia cutting guide head 54 which has been selected and put into position for the appropriate tibial cut. The vertical slide member 34 is permitted to slide with the nut 42 loose until proper alignment and positioning of the members is achieved. Once alignment with the cutting guide head 54 is achieved, the thumb nut 32 may be tightened, leaving the nut 42 loose to permit vertical movement of the slide 34 until proper tension is applied to the ligaments.

With the squaring jig properly fitted to the cutting guide head, the ligaments are distracted to indicate the appropriate tension in the ligaments and the thumb screw 42 tightened. The indicators 57 and 60 are then viewed to ascertain alignment with the appropriate scale on the slide member 34. The alignment of one of the indicator lines 57 and 60 with a line on one of the scales indicates the particular size femoral prosthesis to be selected such as small, regular, large or extra-large. These sizes are also sized according to the appropriate line on the particular scale. This indicates the proper height tibial prosthesis to select as well as the proper cuts to take on the distal femoral condyle.

While I have illustrated and described my invention by means of specific embodiments, it is to be understood that numerous changes and modifications may be made therein without departing from the spirit and scope of the invention as defined in the appended claims.

I claim:

1. A flexion spacer guide for guiding the selection and fitting of a knee prosthesis, said guide comprising:
   a base member for attachment to and for alignment with the axis of a femur, said base member including a first arm for alignment with and attachment to said femur and a second arm substantially perpendicular to said first arm and the longitudinal extent of said femur for attachment to said femur,
   a generally L-shaped support member adjustably mounted on said base member for adjustment longitudinally along said base member and along the axis of a femur on which said base member is mounted and said support member having a transversely oriented support arm for alignment with a tibia positioned in substantially 90° of flexion with respect to said femur on which said base is mounted, and
   alignment and sizing gauge means adjustably mounted on said transversely oriented support arm for indicating the size of prosthesis required for knee joint replacement between said femur and said tibia.

2. The spacer guide of claim 1 wherein said support member includes a first arm having an elongated slot, and
   said first arm of said base member includes a guide pin and a stud for engaging said slot for guiding said support member thereon, and
   a clamp nut on said stud for clamping said support member in selected positions thereon.

3. The spacer guide of claim 2 wherein said sizing gauge includes at least one indicator on said vertically oriented support arm of said support member, and
   a slide member, having at least one scale thereon, adjustably mounted on said vertically oriented support arm for selective alignment of said indicator with said scale.

4. The spacer guide of claim 3 wherein said slide includes at least one slot for engaging guide pins on said support arm, and
   said support arm includes a pair of spaced apart pins for engaging said slot of said slide.

5. The spacer guide of claim 4 wherein:
   said indicator comprises a mark on at least one of said guide pins, and
   said at least one scale comprises a plurality of lines on said slide adjacent said at least one slot.

6. The spacer guide of claim 5 wherein said slide includes squaring means for aiding in positioning a tibia of a leg at a right angle to the femur of the leg.

7. The spacer guide of claim 6 wherein said squaring jig includes an arm extending outward from said slide for engaging and aligning with a tibia cutting guide.

8. The spacer guide of claim 7 wherein said arm extends outward at an angle of between 0° and 10° less than 90° to said slide.

9. The spacer guide of claim 6 wherein said squaring means comprises a jig including an extension of said slide extending at a 90° angle to said support arm for engaging the face of a tibia cutting guide.

10. A spacer guide for aiding in the selection of a knee prosthesis comprising a generally L-shaped support member having a first arm longitudinally alignable with a femur and mountable in fixed relation with respect to said femur, a second vertically oriented support arm extending substantially perpendicular to said first arm across at least a portion of the distal end of said femur, said second arm having extending outwardly therefrom and distally of said femur a threaded stud and at least one guide stud, an alignment and sizing gauge having an elongated slot, said elongated slot being slidably engaged over said studs, said threaded stud being of sufficient length so as to protrude outwardly from said slot, a threaded nut threadable over said threaded stud and engageable with a surface of said gauge adjacent said slot so as to enable the selective fixing of the position of said gauge with respect to said second arm, said gauge including a foot member supportable with respect to a tibial surface associated with said femur when said tibia is at substantially a 90° flexion with respect to said femur, said gauge including indicia adjacent said slot related to the chosen tibia plateau and said guide stud including an indicator line alignable with said indicia upon movement of said gauge with respect to said studs to indicate the appropriately sized prosthesis.

11. The invention of claim 10, further including a further guide stud on said second arm, said further guide stud including a further indicator line alignable with said indicia.

* * * * *